United States Patent [19]

Collins et al.

[11] Patent Number: 5,457,025

[45] Date of Patent: Oct. 10, 1995

[54] METHODS AND COMPOSITIONS FOR PREVENTING INTERFERENCE WITH AFFINITY CAPTURE SCHEMES

[75] Inventors: Mark L. Collins, Holden, Mass.; David Gillespie, Glenmore, Pa.; David V. Morrissey, Middletown, Conn.

[73] Assignee: Amoco Corporation, Naperville, Ill.

[21] Appl. No.: 976,678

[22] Filed: Nov. 16, 1992

Related U.S. Application Data

[63] Continuation of Ser. No. 865,793, Apr. 7, 1992, which is a continuation of Ser. No. 322,419, Mar. 10, 1989.

[51] Int. Cl.$^6$ .................................................... C12Q 1/68
[52] U.S. Cl. .................................. 435/6; 935/77; 935/78
[58] Field of Search ................................ 435/6; 935/77, 935/78

[56] References Cited

U.S. PATENT DOCUMENTS

| | | | |
|---|---|---|---|
| 4,302,204 | 11/1981 | Wahl et al. | 435/6 |
| 4,362,531 | 12/1982 | de Steenwinkel et al. | 436/512 |
| 4,683,194 | 7/1987 | Saiki et al. | 435/6 |
| 4,751,177 | 6/1988 | Stabinsky | 435/6 |
| 4,767,699 | 8/1988 | Varu et al. | 435/6 |
| 4,818,680 | 4/1989 | Collins et al. | 435/6 |

FOREIGN PATENT DOCUMENTS

| | | | |
|---|---|---|---|
| 130523 | 1/1985 | European Pat. Off. | 435/6 |
| 0200057 | 4/1986 | European Pat. Off. | 435/6 |
| 0232967 | 8/1987 | European Pat. Off. | 435/6 |
| 0265244 | 4/1988 | European Pat. Off. | 435/6 |
| 0305145 | 8/1988 | European Pat. Off. | 435/6 |
| 2169403 | 7/1986 | United Kingdom | 435/6 |
| 8706621 | 11/1987 | WIPO | 435/6 |

OTHER PUBLICATIONS

Church et al. PNAS(USA) 81:1991–1995 (4–84).
Maniatis et al. Molecular Cloning: A Lab. Manual, Cold Spring Harbor Lab., 1982.
Wood, W. I., et al., *Proc. Natl. Acad. Sci. USA* 82:1585–1588 (1985).
Morrisey, D. V. and Collins, M. L., *Mol. Cell. Probes England* 3(2):189–207 (1989).

*Primary Examiner*—Stephanie W. Zitomer
*Attorney, Agent, or Firm*—Norval B. Galloway

[57] ABSTRACT

Methods and kits are described that allow the efficient capture and detection of targets employing the dA-dT and related affinity pairs from samples potentially containing large amounts of poly(rA) and/or poly(dA).

6 Claims, 2 Drawing Sheets

FIGURE 1A.

□ Poly(dA)-Oligo(dT)   ● Poly(rA)-Oligo(dT)

Sequence of Oligonucleotide Probes

| Probe | Sequence (5' → 3') |
|---|---|
| 576 | XXX XXX XXX XXX XXX XXX XXX XXX |
| 676 | TCA ATT GCT GCG GTT ATT AAC CAC AAC ACC TTC CT |
| 732 | TCC AAC TGT TGT CCT CTT GTG TAG GGC AGA TTA AC |
| 888 | AAA AAA AAA AAA TGT GTT AAG CAG GAG TAT AGA GTA TTA GCA GTC GT |

X = any of the four nucleotides

METHODS AND COMPOSITIONS FOR PREVENTING INTERFERENCE WITH AFFINITY CAPTURE SCHEMES

This is a continuation of application Ser. No. 07/865,793 filed on Apr. 7, 1992, now abandoned, which is a continuation of application Ser. No. 07/322,419 filed on Mar. 10, 1989 now abandoned.

DESCRIPTION

BACKGROUND

The ability of nucleic acids to form sequence-specific hydrogen bonds or to hybridize with complementary strands of nucleic acids serves as the basis for techniques generally called hybridization assays.

In a hybridization assay, a nucleic acid having a selected sequence is used as a probe to search a sample for a target nucleic acid sequence which is complementary in sequence to the probe; binding of the two sequences is subsequently detected using a variety of known techniques. For example, labelling the hybridization complex formed by the probe and the target makes it possible to detect and, if desired, quantitate the target sequence in the sample.

In some hybridization assays, suitable pairs of a capture probe and a substance having an affinity for the capture probe are used to identify the hybridization complex (target nucleic acid sequence-probe complex) and/or remove it from the sample. For example, a poly- or oligonucleotide whose nucleic acid sequence is complementary to a region of the probe can be used. Suitable pairs of affinity component capture probe can be: poly(dG)-poly(dC) (polydioxriboguanylate-polydeoxyribocytidylate); poly(dA)-poly(dT) (polydeoxyriboadenylate-polydeoxyribothymidylate); and poly(dA)poly(U) (polydeoxyriboadenylate-polyuridylate). One member of this affinity pair can be affixed to a solid phase or solid support, such as a chromatography column, filter, plastic surface, glass etc.

Because all strains of a particular microorganism share a genetic component in the form of nucleic acids susceptible to diagnosis by means of a hybridization assay, such hybridization assays are valuable research medical tools. Detection of specific target nucleic acids make it possible to diagnose bacterial, fungal and vital disease states in humans, animals and plants. Additionally, the ability to probe for a specific nucleotide sequence is of potential use in the identification and diagnosis of human genetic disorders.

A particular disadvantage, however, of the use of nucleic acid hybridization schemes based on use of an affinity pair, such as dA-dT, is the possible interference with assay performance by naturally-occurring substances, such as molecules containing poly(rA) (polyriboadenylate) or poly(dA). Mammalian cells, which are found at various levels in virtually all clinical samples, especially blood, contain about 1 attomole ($1 \times 10^{-18}$ mole) of poly(rA) per cell (T. Maniatis et al., *Molecular Cloning: A Laboratory Manual*, p. 188 (1982)). They also contain about 100 ppm poly(dA) and poly(dT) by weight.

If present at high enough levels, endogenous poly(dA) and especially poly(rA), can compete with dA-containing probes for binding to supports having poly(dT). These compounds can also compete with any dA-tailed probes bound to the target molecule in solution. The result is a diminished assay signal and potentially higher backgrounds. The diminished signal results from reduced binding of probe: target complexes to the solid support. The higher backgrounds arise if the poly(rA)- and/or poly(dA)-containing sequences have a detectable amount of homology with the labeled probe. If the molecule to be detected is a poly(rA) mRNA or otherwise contains poly(rA), the specificity of the hybridization assay is reduced because binding of this molecule to the solid support occurs through the naturally-occurring poly(rA) and not through the highly specific poly(dA)-containing capture probe. Methods that prevent endogenous poly(rA) from binding to supports containing polydeoxyribothymidylic acid (poly(dT) are necessary to detect specific poly(rA)-containing mRNAs or other polyadenylated sequences.

There is presently no method available for effectively reducing,interference from endogenous poly(rA) and poly(dA) sequences in affinity pair hybridization assays. Methods employing finely divided particles can, in principle, block potential signal dimunition from poly(rA) and poly(dA) if enough solid phase is used that all of the target molecules and all of the endogenous poly(rA)- and poly(dA)-containing molecules bind to it. Collins, European Patent Application Number 0 265 244; Soderlund, UK Patent Application Number GB 2169403A; Stabinsky, U.S. Pat. No. 4,751,177. However, the use of such a quantity of solid phase particles can cause an unacceptable increase in the normal level of nonspecific background. Its use can also cause an increase in background if a small amount of labeled probe binds to non-target molecules containing poly(rA) or poly(dA).

These methods of reducing interference from endogenous polynucleotides are of limited utility when capture and detection are done on preferred supports for non-isotopic affinity-pair assays, such as poly(dT)-nitrocellulose and poly(dT)-polystyrene. These supports have only a limited binding capacity of about one microgram or less of polydeoxyriboadenylate(dA-12). M. Collins, European Patent Application No. 0 265 244. Furthermore, these supports can be saturated by poly(A)-containing mRNA present in about one million mammalian cells (based on the estimate of about 1 attomole of poly(rA)-200 per cell in Maniatis et al., supra). Although presently-available methods are useful for isotopic detection on magnetic beads, cellulose, and glass solid supports, nonisotopic affinity schemes on those solid supports have not shown sensitivity comparable to detection on poly(dT)-nitrocellulose and poly(dT)polystyrene. M. Collins, European Patent Application No. 0 265 244. In addition, there are no methods for the elimination of competition for binding to poly(dT) between endogenous poly(dA) and the dA-containing capture probes.

It would be useful to have a method whereby affinity-pair hybridization assays could be performed even in the presence in a sample of potentially interfering polymeric nucleotides and interference by the endogenous polynucleotides could be reduced.

SUMMARY OF THE INVENTION

This invention relates to a method of reducing interference from naturally-occurring polydeoxy- and polyribonucleotides in affinity capture assays, as well as to compositions and kits useful in the method. Polynucleotides which are present in samples assayed using affinity capture techniques and which can interfere with hybridization of homopolymer-tailed capture probes and complementary nucleic acid sequences present on a solid support include poly(rA), poly(dA), poly(U) and poly(dT).

Through use of the method of this invention, interference by endogenous polynucleotides with binding of a probe (referred to as a capture probe) which comprises a homopolymer tail and a nucleotide sequence complementary to a nucleic acid sequence of interest (a target nucleic acid sequence) to a support-bound polynucleotide substratum is reduced by use of compositions and/or selected assay conditions which "tie up" endogenous polynucleotides or in some other manner reduce their binding with complementary homopolynucleotide sequences. The interference is reduced, according to the present method, either by interacting directly with the endogenous polynucleotides (e.g., by binding to them) or by affecting indirectly their ability to hybridize with the capture probes and/or solid support affinity ligands (e.g., by altering assay conditions).

In one embodiment of the present method, oligo(dT) or poly(dT) sequences attached to a solid surface (support-bound polynucleotides are sometimes referred to herein as the "substratum") are presaturated with a dA-tailed capture probe to be used in detecting a target nucleic acid sequence in a sample. As a result, the only way in which a nucleic acid sequence can bind to the solid support is through hybridization with the capture probe. Thus, endogenous poly(rA) and/or poly(dA) sequences cannot bind to the solid support.

In another embodiment of the present method, poly(dT) is affixed to a solid support, such as polystyrene, by means of UV or gamma irradiation. As a result, binding of poly(rA) is substantially selectively inhibited; binding of endogenous poly(dA) is not, however, affected.

In a further embodiment of the present method, chaotropic salts, such as guanidinium thiocyanate (GuSCN) and capture on a poly(dT) polystyrene support are used to drastically reduce the ability of poly(rA) to compete with poly(dA)-tailed capture probes for binding to poly(dT) (affixed to the polystyrene support surfaces).

In another embodiment of the present method, endogenous poly(rA) is removed after the target nucleic acids are allowed to complex with the capture probes, and subsequently bind to the substratum. This poly(rA) is then removed enzymatically, for example, by treating the support (having the probe-target complex bound there to) with RNAase H, which removes polyribonucleotides hybridized with DNA.

In another embodiment of the present method, assay of a sample using a poly(dA)-tailed capture probe is carried out in non-chaotropic salts, such as buffered sodium chloride, with poly(dT) affixed to a polystyrene support. As a result, poly(rA) present in the sample binds poorly to poly(dT) present on the polystyrene support, despite the fact that the two polymers normally associate with considerable avidity in the presence of salts such as sodium chloride. In a still further embodiment of the present method, endogenous polynucleotide sequences, such as poly(dA), are prevented from binding to poly(dT) sites affixed to a solid support and left vacant (available for hybridization) through the loss of preimmobilized (prebound) dA-tailed capture probe. This is effected by combining a small quantity of poly(dT) with a sample to be assayed and allowing hybridization of any poly(dA) sequences present in the sample with the poly(dT) to occur. The sample is subsequently combined with the solid support bearing poly(dT).

The method of the present invention can also be used for the detection of endogenous polynucleotide sequences in samples. In these applications, hybridization of the endogenous polynucleotide to the solid phase is prevented or reduced, using the above-described approaches. The endogenous polynucleotides are, thus, available to bind to one or more specific probes in solution.

This invention also relates to assay kits useful in carrying out the method of this invention. Kits can comprise a vial containing a solid support, such as polystyrene, bearing an affinity compound, such as poly(dT), which is presaturated with a dA-tailed specific capture probe and a chaotropic compound such as guanidinium thiocyanate.

DETAILED DESCRIPTION OF THE INVENTION

The present invention relates to methods and kits for performing nucleic acid hybridization assays and, in particular, to methods and kits for reducing interference by homopolynucleotides or homopolymeric nucleic acid sequences present in biological samples with specific binding or hybridization between homopolymer-tailed capture probes and complementary homopolymeric sequences present on a solid support. Hybridization of endogenous polynucleotide sequences, such as poly(rA), poly(dA), poly(U) and poly(dT), with support-bound sequences is interfered with, according to the present method, in one of several ways; these approaches can be used singly or in combination.

The following is a description of the various embodiments of the method of the present invention, each of which is described further in a subsequent Example. In each case, the present method is carried out 1) in the context of what is referred to as a solid phase affinity pair capture assay or affinity sandwich assay, (which is itself a well-known technique, see, Soderlund, U.K Patent Application GB 2169403A); and 2) in order to reduce (lessen, minimize or eliminate) interference by endogenous nucleic acid sequences (e.g., poly(rA), poly(dA), poly(U), poly(dT)) present in a sample analyzed with hybridization of an affinity pair, such as a poly(dT) sequence and a poly(dA) sequence, whose hybridization is essential for the assay procedure.

Thus, in each case, nucleic acid sequences of interest (target nucleic acids) are captured on a solid support as a result of two hybridization events: hybridization of the target nucleic acids with a capture probe comprised of a nucleic acid sequence complementary to the target nucleic acid sequence and a homopolymeric tail, wherein the capture probe is free (i.e., not immobilized) in the solution, and subsequent hybridization of the homopolymeric tail with a complementary homopolymer substratum which is affixed to the solid support.

Another format is possible in which the capture probe is hybridized to the substratum on the solid support and the immobilized capture probe is then contacted with the sample, and the target nucleic acids are captured by hybridizing with the immobilized capture probes. By "tail" is meant an RNA or DNA sequence that may be added, either synthetically or enzymatically, to the 5' and/or the 3' end and/or to one or more internal nucleotides of the capture probe. Those skilled in the art will realize that a capture probe with a pendant 5' poly(rA) or poly(dA) sequence or a tail sequence pendant from one or more internal sites (not involved in base-pairing) can be made to function in this assay as well as a probe with the more usual 3' pendant "tail" sequence. Generally, the capture probes include a poly(dA) or oligo(dA) tail and a nucleic acid sequence complementary to a target nucleic acid sequence for which a sample is to be analyzed. The homopolynucleotide on the solid support is generally poly(dT) or oligo(dT). As used herein, the term poly(dA) is meant to include oligo(dA) as well. Similarly, the term poly(dT) is meant to include oligo(dT). In each case, interference by endogenous homopolynucleotide sequences with hybridization of the homopolynucleotide tail of the capture probe with the complementary homopolynucleotide present on the solid support is reduced by the present method. That is, the ability of endogenous homopolynucleotide sequences to hybridize with complementary homopolynucleotide sequences with which the sample is contacted is reduced by the present method. As a result, the solid phase assay carried out is more specific and sensitive than would be the case if interference by endogenous nucleic acid sequences were allowed to occur.

There are two general types of approaches used in the present method for reducing interference by endogenous nucleic acid sequences, each of which is described below. The first approach makes use of a selected substance, which is generally a polynucleotide having a homopolymeric tail. The sequence of the tail is complementary to a homopolymeric sequence present on the solid support to which the tailed probe is preferably prebound in such a way as to block the binding of endogenous homopolymers to the solid support. The second approach relies on use of selected conditions during target capture and/or washing. These two approaches can be used alone or in combination, as desired.

In the embodiments of the present method in which a polynucleotide is used to reduce interference, the polynucleotide is generally a homopolymer- tailed capture probe. A sufficient quantity of polynucleotide is added to the solid phase prior to contacting with the sample to reduce the binding to the solid phase of any naturally-occurring nucleic acid sequence in the sample.

Naturally-occurring or "endogenous" nucleic acids capable of interfering with solid phase affinity-pair capture assays are polymeric ribo- and deoxyribonucleotides, such as polydeoxyribo- (poly dA) and polyribo- (poly rA) acids. Interference from other polynucleotides, such as poly(dT) or poly(U) can also be eliminated using the method of this invention. These polynucleotides are found in biological samples that are rich in mammalian cells, such as blood. By "polynucleotide" is meant an RNA or DNA molecule that is customarily 10 or more nucleotides in length. The optimum length must be determined empirically for each application. For rRNA targets and the capture scheme disclosed herein, the optimum length of the capture polynucleotide probe is about 25–35 nucleotides. Other applications require different lengths.

There is no practical upper limit to the amount of endogenous homo-polynucleotide that can be prevented from interfering with nucleic acid hybridization assays by the present invention. This is particularly useful for biological samples that contain large quantities of mammalian cells, such as blood.

In one embodiment of this invention, the polynucleotide tail of a capture probe (e.g., a poly(dA)-tailed probe) is allowed to hybridize to complementary nucleic acid sequences (e.g., poly(dT))affixed to a solid phase, prior to combination of the solid substrate with a sample to be assayed (which generally will contain endogenous, interfering polynucleotides). In this embodiment, the homopolynucleotide-tailed capture probe is "prehybridized" to the solid phase (i.e., hybridized to the complementary homopolynucleotide present on the solid support prior to use in an assay), generally in sufficient quantities to saturate the poly(dT) present on the support. These components are incubated under conditions sufficient for hybridization between complementary nucleic acids (i.e. of the capture probe homopolymeric tail and the homopolymer affixed to the solid phase). The purpose of this "prehybridization" is to render substrata on the solid phase unavailable for hybridization with endogenous poly(rA) or poly(dA) present in the sample. The solid phase (now bearing the capture probe) is separated from the solution containing tailed capture probes.

The use of immobilized capture probes is discussed in copending U.S. Application entitled "Immobilized Oligonucleotide Probes and Uses Therefor" by Collins and Morrissey, Ser. No. 07/902,517, filed concurrently herewith, the teachings of which are incorporated herein by reference. In this and other embodiments of the invention, separation of the solid phase from other components of the assay is accomplished through washing, magnetic separation, centrifugation or filtration methods. The solid phase-capture probe complex is subsequently contacted with a sample to be analyzed for the occurrence of target nucleic acid sequences, under conditions appropriate for hybridization of complementary nucleic acid sequences to occur. This results in formation of a solid phase-capture probe-target nucleic acid sequence product. This product is detected using known techniques. This embodiment is described in greater detail in Example 2.

Alternatively, prehybridizing of dT-tailed probes to poly(dA) or poly(rA) solid supports makes it possible to reduce interaction of poly(dT) tailed probes with endogenous poly(rA) and poly(dA) sequences.

As described in Example 3, target Campylobacter rRNA was captured onto poly(dT)-polystyrene using the preimmobilized Campylobacter-specific dA-tailed capture probe #732 in the presence and absence of added poly(dA). Salmonella rRNA was labeled with a generic riboprobe and hybridized to a dA-tailed Salmonella-specific oligonucleotide in solution in order to determine if this labeled poly(dA)-containing molecule would decrease the assay signal or increase the assay noise.

Results presented in Example 3 show that the poly(dA)-containing molecules did not decrease assay signal development when target capture was done using poly(dT)-polystyrene containing a prehybridized Campylobacter-specific dA-tailed polynucleotide. It is further shown that this result is due to the failure of the poly(dA)-containing molecule to actively displace the Campylobacter dA-tailed probe from the poly(dT). The current state of the art would not allow one to predict that the exogenously added poly(dA) would not in fact displace the prebound tailed probe. Certainly, at equilibrium, there would be a considerable amount of displacement because the equilibrium constant for the displacement of a shorter, dA tailed prebound probe by a longer dA tailed, exogenously added probe would be expected to be slightly greater than one. Evidently, equilibrium is not reached under these incubation conditions.

The fact that the Campylobacter probe was retained equally well in the presence and in the absence of exogenous poly(dA) demonstrates that this technique of pre-binding the dA-tailed capture probe to poly(dT) supports is useful in preventing any possible loss of signal caused by endogenous poly(dA) and poly(dT) during the capture of target nucleic acids, such as Campylobacter rRNA with dA-tailed oligonucleotide probes.

It is also possible to use the method of the present invention to selectively prevent interference by endogenous polyadenylate nucleotides, such as poly(rA). In particular, interference from poly(rA) present in the biological sample can be eliminated by performing the capture assay under conditions that selectively prevent the binding of endogenous poly(rA) to homopolynucleotides or substrata on the solid phase.

By "substratum" is meant a layer of a material that is laid down on a solid support by covalent or noncovalent means. The substratum greatly enhances the binding of the next layer of material. There can be many layers of substrate bound to the first solid phase. For example, poly(dT) can be bound to polystyrene. Polymeric nucleotides tailed with (dA) and carrying a multiplicity of second affinity ligands can be bound to the poly(dT) substratum. Other materials can be bound to each of the second affinity ligands on each of the tailed first oligomers, etc., building up a vast three-dimensional array of capture sequences that would be able to capture a target rapidly and efficiently.

The selective inhibition of poly(rA) binding to substratum on a solid phase in affinity assays of this invention is based on several discoveries, which are described in Example 2. It has been discovered that both poly(rA) and poly(dA) will differentially bind to poly(dT) in the presence of certain salts. In particular, it has been discovered that poly(rA) will not compete with a poly(dA)-tailed capture probe for hybridization to a poly(dT)-solid support, either when the capture probe is added in solution or when the capture probe is pre-hybridized to a poly(dT)-bearing solid support. This is due, in part, to incubation of these components in the presence of a chaotropic compound. In this context, a chaotropic compound is one that denatures molecules, primarily through disrupting the water lattice surrounding the molecule. Hamaguchi, K. and Geiduchek, E. P. *J. Am. Chem. Soc.*, 84 1329–1338 (1962). A particularly preferred chaotropic compound useful in methods of this invention is the chaotropic salt, guanidinium thiocyanate (GuSCN). Other preferred chaotropic salts are the monovalent salts of large acid ions such as trichloroacetate (TCA), trifluoroacetate (TFA) and thiocyanate (SCN). Thus, an unexpected discovery is that use of chaotropic salts, in particular GuSCN, can prevent competition between poly(rA) and poly(dA)-tailed capture probes for binding to dT-containing solid supports.

A further unexpected result is that poly(rA) hybridizes very poorly to substratum affixed to polystyrene (e.g., poly(dT)-polystyrene). The mechanism for this binding inhibition is not clear. Results presented herein show that poly(rA) does not hybridize to polystyrene having a poly(dT) substratum, even in buffers containing sodium chloride (NaCl), and that this unexpected result can be used to prevent interference from endogenous polyadenylated molecules in solid phase, affinity pair capture assays. Poly(dT)-polystyrene can also be used in conjunction with a chaotropic compound, such as GuSCN, to further reduce the ability of poly(rA) to compete with poly(dA)-tailed capture probes for binding to poly(dT).

The use of appropriate concentrations of chaotropic compounds, such as GuSCN, combined with suitable temperatures, during affinity capture assays is equally useful with a capture probe containing a tail of polydeoxythymidylate (poly(dT)) and a solid phase to which is affixed poly(dA). This is so because endogenous poly(rA) will not be able to bind to the poly(dT) tail of the capture probe, thus leaving the poly(dT) tail free to bind to the poly(dA) on the solid support.

Three variables are important in the present method: the concentration of the chaotropic salt (e.g., GuSCN), temperature and the length of the probes. For example, temperature can vary from about 0° C. to about 100° C. The concentration of GuSCN (or other chaotropic salt) can be from about 0.25M to about 4M. The probe length can be from about 10 to about 3000 nucleotides. As the length of the probes is increased, the temperature at which poly(rA) can be inhibited from binding, or the concentration of chaotropic salt, or both, should be increased. A preferred temperature range for the present method is from about 4° C. to about 65° C.; with 37° C. being a particularly useful temperature. For example, a concentration of GuSCN of about 2.5–3.5M at about 37° C. is useful for inhibiting interference by poly(rA) with poly(dT)-poly(dA) pairing; and a concentration of about 1.0–1.5M GuSCN at about 37° C. is useful for inhibiting interference with oligo(dT)$_{14}$-poly(dA) pairing. However, many combinations of temperature, chaotrope concentration and probe length are possible, and the best combination can easily be determined empirically.

In another embodiment of the method of this invention for preventing interference by endogenous polynucleotides with affinity capture assays, chaotropic salts and other suitable compounds are used to selectively remove endogenous polynucleotides which hybridize with a complementary homopolymer bound to a solid support.

As described in Example 2, an alternative method of preventing poly(rA) interference in affinity pair capture assays has been developed, based on washing of solid support-bound polynucleotides with an appropriate buffer or other liquid containing a reagent capable of selectively removing (washing off) bound polynucleotides. In this embodiment, although both poly(rA) and poly(dA) bind to the solid support, a buffer containing a reagent, such as GuSCN, is used to selectively wash poly(rA), but not poly(dA), from (dT) substrate (i.e., (dT)-containing supports).

Other reagents such as RNAse H, which selectively digests the RNA sequences in an RNA/DNA hybrid (Berkower, et. al., 1973. *J. Biol. Chem.*, 248:5914; Vournakis, J. H. et al., 1975. *Proc. Natl. Acad. Sci. USA* 72: 2959), can be used to selectively wash the poly(rA) containing sequences from a poly(dT)- containing support. These reagents can be used either singly or in various combinations. A preferred method of using RNAse H and GuSCN is to to use RNAse H in one wash step and then to use GuSCN to remove poly(rA) sequences in another wash step. The use of two methods that work by different and independent mechanisms is preferred because the efficacy is usually much greater than is the case with a simple repetition of the same method or the use of methods that work by the same mechanism. One skilled in the art will further realize that a combination of selective binding of poly(dA) to a poly(dT)-containing support and selective elution of the vast majority of any remaining poly(rA) from the support during washing can be effectively employed as well.

It is also possible, using the present method, to prevent endogenous polynucleotide sequences (e.g., poly(dA)) from binding to polynucleotide sites (e.g., poly(dT)) which are affixed to a solid support and left available for hybridization with a complementary sequence (vacant) through the loss of a small amount of preimmobilized homopolymer-tailed (e.g., (dA)-tailed) capture probe. As described in Example 4, prior to being contacted with a solid support bearing a polynucleotide (e.g., poly(dT)), the sample is combined with a small quantity of the same polynucleotide (here, poly (dT)) as that affixed to the solid support and maintained under conditions appropriate for hybridization of complementary nucleic acid sequences to occur. The quantity of polynucleotide used should be an excess over what is sufficient to bind the endogenous polynucleotide sequences; the precise quantity must be determined for a particular sample type. Subsequently, the sample is contacted with the solid support bearing poly(dT), and capture probe attached thereto.

The present methods of preventing interference with polynucleotides in nucleic acid hybridization assays can be used to advantage as a means of detecting the endogenous polynucleotide. That is, methods described herein can also be used to gain additional specificity in hybridization reactions wherein targets contain polymers of A, T or U. By blocking binding of the endogenous polynucleotide to the substratum on the support, the target, if present, must bind to the solid support through the polymeric tail on a specific capture probe (to which the target must be specifically hybridized). In particular, the method provided herein allows for the specific detection of a polyadenylated target by blocking the binding of the target to a (dT)-containing solid phase through its own polyadenylated sequence and forcing it to bind to the solid support through a specific tailed capture nucleotide to which the target must specifically hybridize.

Additionally, by labeling the target (e.g., endogenous polynucleotide) with a specific labeled (reporter) probe, the present invention provides a method for detecting the target containing polymeric sequences that is dependent on the specific hybridization of two probes to the target. These methods are generally useful with targets containing polymeric sequences and are particularly useful with "chimeric" polyadenylated mRNAs. Chimeric mRNA is a single uninterrupted chain of ribonucleic acid nucleotides that consists of sequences that are normally or usually found or can in certain cases be found in two or more separate and distinct RNA molecules; alternatively, a chimeric mRNA refers to a single uninterrupted chain of ribonucleic acid nucleotides whose DNA coding sequences are formed prior to transcription by a recombinational event(s) between two or more different DNA coding sequences prior to transcription. In this case, to establish the chimeric nature of such mRNAs, it is crucial to observe that two normally distinct polynucleotide sequences have become joined into one molecule. A specific capture probe binding to one sequence and a specific reporter probe binding to the other sequence will suffice to establish whether the two sequences have been joined into one.

For example, a method of detecting a polyadenylated nucleic acid in a biological sample comprises formation of a hybridization complex between the polydenylated nucleic acid and complementary sequences on a capture probe which is affixed to a (dT) substratum on a solid support. The polyadenylated target nucleic acid can be prevented from binding to the poly(dT)-containing solid support using the methods previously described. That is, capture probes can be prehybridized to the solid phase prior to contact of the solid phase with the sample containing the target. Alternatively, any poly(rA)-containing target can be incubated in the presence of a chaotropic salt to prevent its binding to the solid phase, as described previously.

Any of the methods previously described to inhibit binding of endogenous polynucleotides can also be used to detect polynucleotides using reporter and capture probes. For instance, a hybridization complex is formed of the target nucleic acid sequence, a capture probe and a labeled probe. Both the capture probe and the labeled probe are capable of hybridizing to the target nucleic acid. If the target polynucleotide contains, for example, a trace of poly(rA), its direct binding to the dT substratum on the solid phase can be blocked using methods of this invention. The poly(rA) target polynucleotide bound to its reporter probe must bind to the solid support through complementary sequences on the capture probe only.

Kits containing materials to be used in the present method for preventing polynucleotide interference in affinity-pair assays are also the subject of the present invention.

Such kits can include, for example, vials, or other containers, which contain a capture probe having a homopolymer tail, a solid phase to which is affixed a polynucleotide complementary to the tail on the capture probe, a chaotropic agent and, optionally, reagents to be used for preventing hybridization of complementary sequences and/or for selectively removing (washing off) hybridized sequences. For example, a kit designed to prevent interference from poly(rA) can contain:

a. a vial containing a chaotropic salt such as GuSCN;

b. a vial containing one or more (dA)-tailed capture probes, the probes being specific for the targets; and c. a container comprising a special solid support (e.g., dipsticks or microtiter wells) to which poly(dT) is affixed in such a way as to inhibit the binding of poly(rA).

Alternatively, a kit can contain the vial in (a) and a second vial containing a solid support bearing poly(dT) as the substratum and a prehybridized selected capture probe. Endogenous poly(rA) which binds to the substratum can be removed by an enzyme specific for the RNA of an RNA-DNA duplex, such as RNAase H, after the binding of the target to the probe, and subsequent binding of the probe-target complex to the support. Kits can be designed so that the presence of any species within a genus can be detected, for a specific disorder. For example, a kit can be designed having capture probes specific for Salmonella, Shigella or Campylobacter. Alternatively, a kit can be designed, for testing gastrointestinal disorders, which contains probes specific for all three of these types of bacteria.

The kit can, optionally, contain one or more of the following: a labeled probe for detecting and quantifying the target nucleic acids, a means for detecting the labeled probe, wash buffers (e.g., for reducing non-specific binding), one or more elution buffers, amplification or cloning reagents, and/or one or more positive control samples, and one or more negative control samples. Amplification of the target sequences can be accomplished, for example, by the technique described by Mullis in U.S. Pat. No. 4,683,202. Cloning of the isolated target can be accomplished by the methods described by Maniatis et al., *Molecular Cloning: A Laboratory Manual*, Cold Spring Harbor, N.Y. (1982). The labeled probe can be labeled, for example, with fluorophors, ligands (such as biotin or antigens) chemiluminescent compounds or radioisotopes. The means for detecting the labeled probe will depend upon the type of label used; for example, radionuclide label can be detected by autoradiography, or scintillation counting.

This invention will now be more fully described with reference to specific examples, which are not to be construed as limiting in any way.

Example 1

Methods of Preparing Probes and Solid Supports

This example illustrates general materials and methods used to prepare the components of this invention.

A. Tailing of Capture Probes

Oligonucleotide probes were tailed overnight at 37° C. in 0.1M potassium cacodylate (pH 7.0), 4 mM MgCl, 1 mM 2-mercaptoethanol, 0.1 mg/ml acetylated bovine serum albumin (BSA), dATP oligonucleotide at a 30:1 to 100:1 molar ratio, and 1000 units per ml of TdT (Supertechs). A small amount of tritium labeled dATP was added to monitor tail length and binding of the probes to the polystyrene.

B. Preparation of Labeled Probes

Labeled riboprobes: A 3' 720 bp fragment of the *E. coli* 16S rRNA was cloned into the pGEM4 vector. (Promega Biotec) It was transcribed with SP6 polymerase using bio-11-UTP (Enzo) according to the manufacturer's instructions (Promega Biotec). The riboprobe was then purified by two rounds of ethanol precipitation.

Alternatively, a 5' 567 bp fragment of the *E. coli* 16S rRNA was cloned into the pGEM4 vector. It was transcribed with T7 polymerase using bio-11-UTP (Enzo) according to the manufacturer's instructions. The riboprobe was then purified by two rounds of ethanol precipitation.

These probes are capable of hybridizing through short stretches of homology to all eubacterial 16S rRNA for which sequence information is available. They have been shown to hybridize to *E. coli*, Shigella, Salmonella, Campylobacter, Listeria, *Neisseria gonorrhea*, and *Chlamydia trachomatis*.

C. Coating of Polystyrene with Poly(dT)

The following procedure is specifically tailored to microtiter wells, but with a few modifications it can be successfully employed for binding polymers of dT to gamma irradiated dipsticks (Hygeia, In., Newton, Ma.) and polystyrene tubes.

A volume of 0.3 ml of 3 OD/ml poly(dT) in 1.5M NaCl, 0.3M Tris pH 8.0, 0.5M $MgCl_2$ per microtiter well (Dynatech Immulon 2) was incubated and sealed overnight at 37° C. The dT mixture was then removed from the wells, which were dried at 37° C. for 30 minutes. The dried wells were exposed to 650 $\mu W/cm^2$ of UV (254 nm) for 2 minutes, washed three times with 1M NaCl, 100 mM Tris pH 9.3, 2 mM $MgCl_2$, 0.1% Tween-20, and air dried. Wells were blocked with 2.5M guanidinium thiocyanate (GuSCN), 2.5% acetylated BSA, 10 µg/ml *E. coli* ssDNA, 10 mg/ml tRNA for 1 hour at 37° and washed three times as above. Wells were dried, sealed well, and stored at room temperature until use. There was no loss in binding capacity after three months of storage with this procedure.

To determine the binding capacity of the poly(dT) coated wells, 0.3 ml of $^{32}P$ 5' end-labeled dA12 (5 µg/ml) was added per well and incubated for 15 minutes at room temperature. The wells were washed three times with the above buffer and then scintillation counted. An acceptable dA12 binding capacity was determined to be greater than or equal to 250 ng/well.

Example 2

Prehybridization of Polynucleotide Tailed Capture Probes to Solid Phase

A. Binding of dA-tailed oligonucleotide probes to poly(dT) coated microtiter wells prior to target capture A binding mixture of 2.5M GuSCN, 200 mM Tris pH7.4, 40 mM EDTA, 2.5% acetylated BSA, and 2.5 µg/ml of the dA-tailed probe was added to preblocked microtiter wells with and without (negative control) dT3000 coating. The mixture was incubated at 37° C. for one hour and removed from the wells. The mixture was saved. The wells were washed three times with the standard wash buffer. Both selected wells and the used binding mixture were scintillation counted. To determine the amount of tailed probe bound to the wells, the following formula was used with C defined as capacity in micrograms:

$$C = \frac{\text{cpm added} - \text{cpm removed}}{\text{Specific Activity of the probe (cpm/µg)}} = \frac{\text{cpm bound}}{\text{Specific Activity (cpm/µg)}}$$

The two methods used to calculate capacity were in excellent agreement. Control wells which were not coated with polydeoxythymidylate bound an average (N=5) of 1 ng of tailed probe. Poly(dT) wells typically bind 300–500 ng of tailed probe, depending on the tail length.

B. Use of pre-bound capture probes in a nonisotopic assay

Capture probes can be immobilized either on polystyrene microtiter wells, polystyrene tubes or dipsticks, with all supports functioning equally well for assaying clinical samples. The following procedure is tailored specifically for use with polystyrene microtiter wells. However, with alterations in volumes, it has been easily adapted to dipsticks and tubes.

Three volumes of 1.3X processing buffer (3.25M GuSCN SCN, 0.4M Tris pH7.5, 008M EDTA, 13% dextran sulfate, 1% Sarkosyl) were added to the samples. After vortexing for 30 seconds, 300 µl of sample was added to each microtiter well and capture of endogenous polynucleotide by the pre-bound capture probe was allowed to occur for L minutes at 37°, where L is the length of the tail on the capture probe. The optimum tail length has been found to be 30–50 nucleotides and the optimum capture time about 30–50 minutes. The samples were then removed from the wells, and the wells washed with 2.4M TEA Cl for 15 minutes at 37° C. This was followed by a series of three washes with 1M NaCl, 0.1M Tris pH 9.3, 2 mM $MgCl_2$, 0.1% Tween-20. A 300 µl volume of a biotinylated generic riboprobe mixture was added to each well and incubated for 30 minutes at 37° C. This mixture contained 0.5–1.0 µg/ml of the riboprobe, 2.5M GuSCN, 0.2M Tris pH7.5, 0.01M EDTA, and 10% dextran sulfate. The riboprobe mixture was then removed from the wells, which were washed three times with the above NaCl buffer. A streptavidin-alkaline phosphatase conjugate diluted 1:500 was added to the wells (300 µl/well) and incubated for 10 minutes at room temperature. This was followed by three to five washes with the NaCl wash buffer and then the addition of the enzyme substrate pNPP (1 mg/ml) in 1x diethanolamine buffer (Kirkegaard and Perry, Gaithersburg, Md.). The optical density at 405 nm was read when the background on the negative control wells started to appear.

C. Use of capture probes free in solution in a nonisotopic assay

The dA-tailed capture probe and the biotinylated generic riboprobe were both added at 0.5 µg/ml to the cell extracts in 2.5M GuSCN buffer containing 10% dextran sulfate. The resulting solution is incubated for one hour at 37° C. in poly(dT)-wells (or dipsticks). The solid supports were washed with the NaCl wash buffer. A streptavidin-alkaline phosphatase conjugate (BRL) was diluted 1:500 in 1M NaCl, 0.1M Tris-HCl (pH 7.5), 5 mM Magnesium chloride (MgCl$_2$), 0.1 mg/ml single-stranded *E. coli* DNA and 0.5% acetylated BSA, and incubated in the wells for ten minutes at room temperature. The wells were washed three times with 1M NaCl, 0.1M Tris-HCl (pH 9.3), 5 mM MgCl$_2$, 0.1% Tween-20. Color was developed with 1 mg/ml pNPP in 1× diethanolamine (Kierkegaard and Perry) until the background became visible. Color was quantitated by OD at 405 nm on a microtiter plate reader (Titertek or Dynatech).

Figure 2:
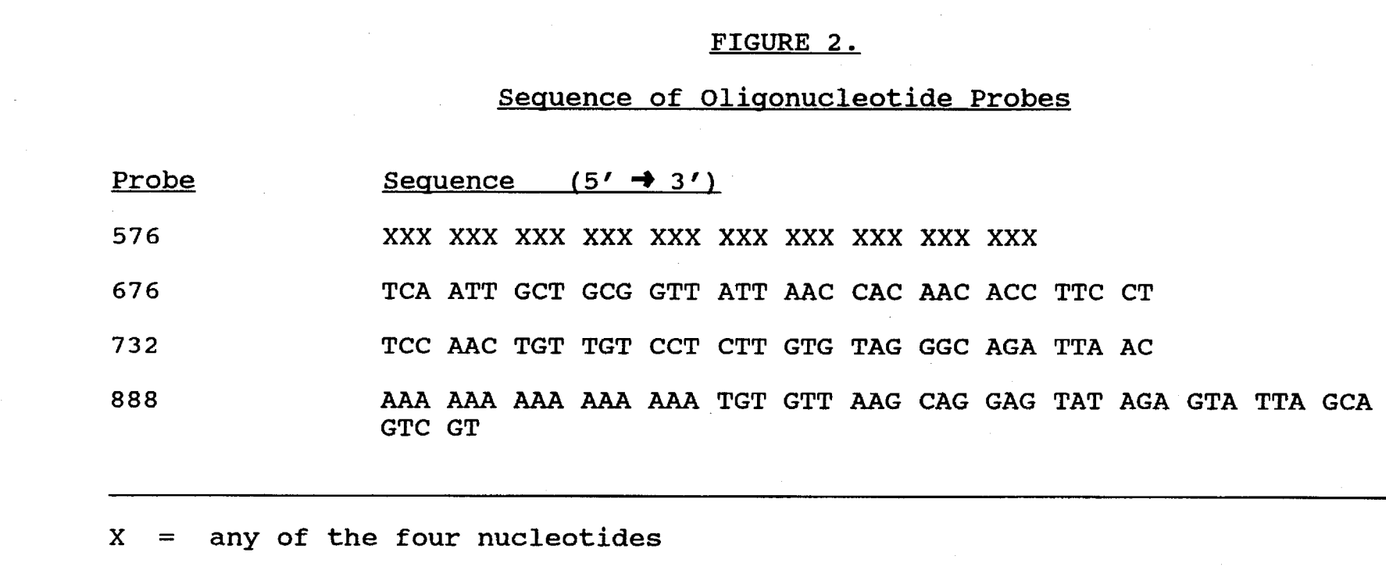
FIG. 2 is a schematic representation of the nucleotide sequence of selected oligonucleotide probes used in the present invention.

Data are presented from two representative experiments comparing the results employing either the preimmobilized capture probe or the capture probe free in solution. Campylobacter specific capture probe #732 (dA65) (FIG. 2) was used to assay Campylobacter extracts (5×10$^6$ cells/ml) in the presence or absence endogenous polynucleotide. Poly (dT) coated polystyrene dipsticks were used as the substratum and solid support, respectively, for the capture of target molecules.

Two situations are considered: no competitors present (5×10$^6$ Campylobacter only) and competitor poly(rA) present at 10 μg/ml. This is the amount of poly(rA) that would be present in 1×10$^8$ mammalian cells/ml, which is the practical limit for mammalian cells in a sample because of viscosity limitations on the ability of samples solubilized in GuSCN to be transferred using a pipette. Barring displacement of the tailed probe by the poly(rA), one might predict that in the presence of competitor, the preimmobilized probe format would show little or no lost signal, while the format with the probe free in solution would show a substantial signal loss. Surprisingly, however, poly(rA) did not compete with the tailed probe-target complex for binding to the poly(dT)-polystyrene, even when the tailed probe was added free in solution. The data substantiating this are presented in Table 1.

TABLE 1

Comparison of Competitor Effects on Solution and Immobilized Assay Formats

| Sample | OD 405 nm | |
|---|---|---|
| | Solution | Immobilized |
| Exp. 3A | | |
| Campylobacter | 1.209 | 1.044 |
| Campylobacter + poly (A) | 0.932 | 1.439 |
| Exp. 3B | | |
| Campylobacter | 0.962 | 0.796 |
| Campylobacter + poly (A) | 1.086 | 0.949 |

The failure to observe competition between poly(rA) and the dA-tailed probes was explained by the following experiments. Aliquots of 5' end-labeled poly(rA)-400 and poly(dA)-50 were added to microtiter wells coated with poly(dT)-4000 in the indicated salt solutions and incubated for 15 minutes at 37° C. All solutions also contained 0.1M Tris-HCl (pH 7.5, 0.01M EDTA, 0.5% Sarkosyl, 0.2% BSA, and 0.04% bronopol. The plates were washed with the indicated buffers once and counted in a Beckmann L1801 Liquid Scintillation Counter. The CPM from the 5M GuSCN have been subtracted as a background value from all numbers except those on the beads. Results in Table 2 show that: (1) poly(dA) binds well but poly(rA) binds very poorly to poly(dT) in 2.5M–3.0M GuSCN at 37° C. and (2) poly(dT)-polystyrene binds poly(rA) poorly even under conditions normally conducive to the association of that affinity pair (e.g., in 0.5M NaCl).

TABLE 2

| | CPM Bound | |
|---|---|---|
| Buffer | poly (rA) | poly (dA) |
| The Binding of Poly (rA) to Poly (dT) Polystyrene | | |
| 0.5 M NaCl | 69,000 | 522,000 |
| 0.5 M GuSCN | 92,000 | 642,000 |
| 1.0 M GuSCN | 65,000 | 676,000 |
| 1.5 M GuSCN | 61,000 | 642,000 |
| 2.0 M GuSCN | 31,400 | 618,000 |
| 2.5 M GuSCN | 0 | 459,000 |
| 3.0 M GuSCN | 0 | 431,000 |
| 5.0 M GuSCN | 0 | 0 |
| Control experiments: Binding of poly (rA) to magnetic beads having (dT) substratum | | |
| 0.5 M NaCl | 372,250 | N.D. |
| 1.0 M GuSCN | 12,300 | N.D. |

An amount of poly(rA) was added (8 ng) that is far less than the capacity of the microtiter wells (about 350 ng), yet only a few hundred picograms of poly(rA) bound to the plates in the 0.5M NaCl buffer control. This result was checked two more times with the exact same result. The binding of poly(dT) to polystyrene must somehow also inhibit the binding of poly(rA) to poly(dT) because the controls showed that almost all of the poly(rA) bound to (dT) magnetic beads in the same 0.5M NaCl buffer. The failure of poly(rA) to bind to poly-(dT)-polystyrene in a buffer in which the two polymers normally associate readily is novel and unexpected. It can be used as the basis for capture schemes making use of affinity pairs (e.g., dA-dT) in samples which contain significant numbers of human or other cells which contain large numbers or polyadenylated molecules.

The use of reagents, such as approximately 2.5–3.0M GuSCN, coupled with capture on poly(dT) polystyrene at 37° C., drastically reduced the ability of poly(rA) to compete with poly(dA) tailed probes (potentially bound to target) for binding to poly(dT) such that no loss of signal was observed at all (Table 1). One skilled in the art will realize that other combinations of temperatures, chaotrope concentrations and hybrid length could be used to accomplish such selective binding of poly(dA) to poly(dT).

The use of GuSCN to bind poly(dA) but not poly(rA) polymers to dT supports was further investigated using poly(dT) magnetic supports. See, Collins, European Patent Application Number 0 265 244, herein incorporated by reference. Poly(rA)-400 and poly(dA)-50 were 5' end-labeled and aliquots were incubated for 5 min at 37° C. with magnetic beads in either 0.5M NaCl (control) or 0.25M, 0.5M, 0.75M, 1.0M, 1.25M, and 1.5M GuSCN. All buffers contained 0.1M Tris-HCl, pH 7.5, 0.01M EDTA, 0.2% Sarkosyl, 0.2% Fraction V BSA, 0.04% bronopol. The beads were washed twice with the indicated buffer at 37° C. and counted. The results are shown in FIG. 1A.

Figure 1A:
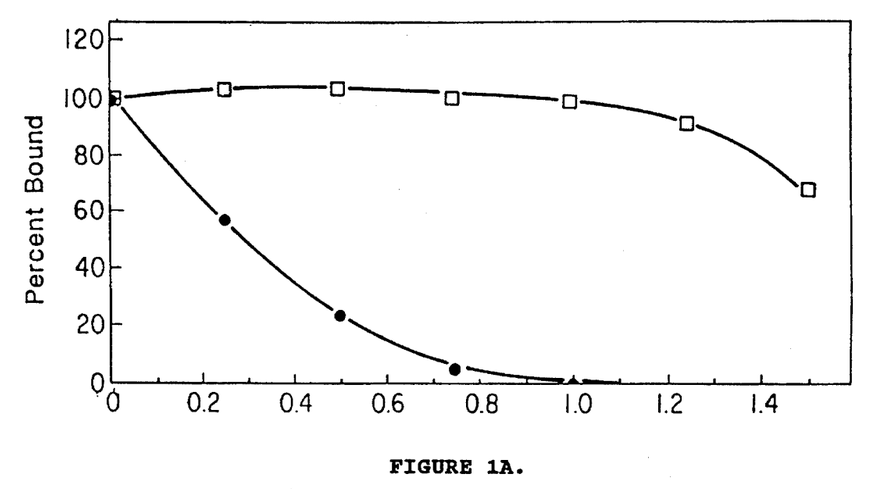
FIG. 1A is a graphic representation of the binding of poly(rA) and poly(dA) to oligo(dT) as a function of the concentration of GuSCN in the binding mixture.

As shown in FIG. 1A, poly(rA)-400 binds well to magnetic beads in 0.5M NaCl, but very poorly (1%) in GuSCN at 1.0M or above. Poly(dA) binds about as well (100%) to magnetic beads in 1.0M GuSCN as in 0.5M NaCl, but gradually loses the ability to bind at higher GuSCN concentrations. Thus, by capturing polynucleotides on the targets in a solution containing about 1M GuSCN at 37° C., endogenous poly(rA) can be effectively blocked from binding to the (dT)$_{14}$ beads. Thus, poly(rA) will not compete for binding sites with dA-tailed probes potentially bound to targets in about 1.0M GuSCN, but is able to compete in 0.5M NaCl. The use of approximately 1.0M GuSCN for selective binding of poly(dA) to oligo(dT)$_{14}$ beads is unexpected.

Figure 1B:
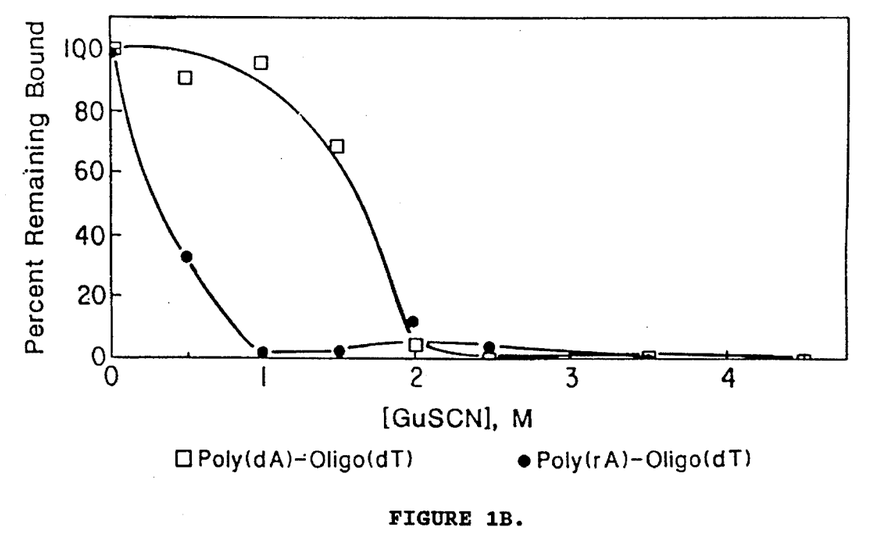
FIG. 1B is a graphic representation of the stability of poly(rA)-oligo(dT) and poly(dA)-oligo(dT) double helices as a function of the concentration of GuSCN in the wash buffer.

To see if the poly(rA)-(dT) helix is simply unstable in 1.0M GuSCN or if the rate of formation of this helix is just unusually slow, poly(rA) was bound to (dT) containing beads in the 0.5M NaCl buffer and washed twice with the various GuSCN buffers at 37° C. The results are shown in FIG. 1B.

The data are essentially indistinguishable from the data of FIG. 1A: At 0.5M GuSCN, only 32% of the poly(rA) remains bound to the beads and at 1.0M GuSCN less than 1% of the poly(rA) remains bound to the beads. The 1.0M GuSCN wash removed virtually none (less than 5%) of the bound poly(dA). Thus, washing the beads as described in approximately 1.0 M GuSCN is sufficient to selectively remove poly(rA)-containing sequences while retaining virtually all of the poly(dA)-containing sequences. The data show that the poly(rA)-oligo(dT) helix is simply unstable in 1.0M GuSCN. Perhaps the poly(rA) can form an intramolecular secondary structure in 1.0M GuSCN involving hundreds of "base pairs" that is far more stable than the short base-paired competing structure, oligo(dT)oligo(rA). Upon formation of this putative secondary structure, the (dT)-containing magnetic bead would be displaced by the poly(rA) folding back upon itself.

Other combinations of chaotrope concentration, temperatures, and length of hybrid can be used to accomplish this selective hybridization of poly(dA) to poly(dT).

Example 3

Inhibition of Interfering poly(dA) Containing Molecules Using Pre-hybridized Capture Probes
A. Materials and Methods The protocol for these experiments was as follows:

To poly(dT)-polystyrene wells that were prehybridized with $^{32}$P-labeled Campylobacter-specific tailed probe (tail length 65; see Example 2) were added:

A. No tailed probe, 4×10$^6$ Campylobacter/ml.

B. Salmonella-specific tailed probe (0.5 µg/ml), 4×10$^6$ Campylobacter/ml.

C. No tailed probe, 1×10$^6$ Salmonella/ml.

D. Salmonella-specific tailed probe (0.5 µg/ml), 1×10$^6$ Salmonella/ml.

The wells were incubated at 37° C. for 40 minutes with 0.5 µg/ml of the 5' biotinylated riboprobe, which labeled both Salmonella and Campylobacter rRNA. Then all supernatants were counted to determine the amount of tailed Campylobacter specific probe that eluted from the support in A through D. At that point color was developed to measure signal strength in all samples.

As seen in Table 3, the retention of the tailed Campylobacter probe in samples A through D was excellent and was not influenced by the presence or absence in solution of the poly(dA)-tailed Salmonella probe. The total amount of exogenously added poly(dA) was 1.6 µg/ml. This is the amount of poly(dA) contained in 3×10$^9$ mammalian cells/ml. The practical limit for use of mammalian cells in an assay is only 1×10$^8$/ml because of viscosity limitations on pipetability.

TABLE 3

Retention of Campylobacter Probe Pre-hybridized to the Poly (dT)-polystyrene in the Presence and Absence of Added Salmonella Tailed Probe:

| Sample | Tailed Probe Added Exogeneously | CPM Supernatant | CPM Wells |
|---|---|---|---|
| A. | No | 2767 | 46792 |
| B. | Yes | 3104 | 42751 |
| C. | No | 2243 | 42715 |
| D. | Yes | 2228 | 45963 |

The results shown are the average of triplicates. In all cases more than 93% of the tailed probe prehybridized to the wells was retained. This shows that there is no active displacement of the Campylobacter probe (tail length 65) by the addition of Salmonella probe 676 (tail length 110) (FIG. 2) at 0.5 µg/ml and incubation in 2.5M GuSCN for 40 minutes at 37°.

Table 4 shows that the signal (color) obtained by the capture of 4×10$^6$ Campylobacter is the same whether poly(dA) is added or not. Backgrounds (no Campylobacter) were small in both cases.

TABLE 4

Effect of Exogenously Added Poly (dA) on the Detection of Campylobacter Target rRNA:

| Sample | Exogenously Added Tailed Probe | OD405 |
|---|---|---|
| A. | No | 0.895 |
| B. | Yes | 0.928 |
| C. | No | 0.000 |
| D. | Yes | 0.017 |

The color produced in A and B (Table 4) was very similar after correction for background (C and D). This shows that the presence of the exogenously-added Salmonella tailed probe produced no adverse effect on signal and produced only a slight increase in background. This slight increase in background is probably due to a small amount of labeled Salmonella rRNA binding through the Salmonella tailed probe to poly(dT) left exposed by the loss of 6–7% of the prebound Campylobacter probe shown in Table 3. This increase in background is an artificial upper limit since labeled probe is highly complementary to a polyadenylated sequence, in this case a nontarget rRNA that is polyadenylated by virtue of a capture probe that can bind to the solid phase. More likely, in routine use the endogenous polyadenylated species would have little or no homology to a labeled nucleotide probe specific for the analyte of interest. Thus, the background resulting from a small amount of this polyadenylated species binding to the solid phase would be very small since, for the most part, the polyadenylated material would be unlabeled.

The method of prehybridizing a tailed capture probe to complementary nucleotides (i.e., substrata) on a solid support will prevent interference with the capture of nucleic acids that are to be detected, not only from endogenous poly(dA) but also from poly(rA), poly(U) and poly(dT) as well as the corresponding oligomeric sequences. The probes could be tailed with poly(dA), poly(rA), poly(U) or poly(dT) or any of the corresponding oligomeric sequences.

Example 4

Simultaneous Use of Prehybridized Capture Probe and Polynucleotide in Solution to Inhibit Endogenous Polynucleotides This example illustrates a method whereby endogenous poly(dA) can be prevented from binding to vacant poly(dT) sites left by the loss of a small amount of prehybridized dA-tailed probe. In this example, an amount of poly(dT) is added to the specimen in solution and allowed to hybridize to the endogenous poly(dA) in the presence of the prehybridized solid phase.

Materials and Methods

The protocol for these experiments was similar to Example 3:

To poly(dT)-polystyrene wells that were prehybridized with $^{32}$P-labeled Campylobacter-specific tailed probe (tail length 65) were added:

A. No tailed probe, $4 \times 10^6$ Campylobacter/ml.

B. Listeria-specific tailed probe (0.5 μg/ml), $4 \times 10^6$ Campylobacter/ml.

C. No tailed probe, $1 \times 10^6$ Listeria/ml.

D. Listeria-specific tailed probe (0.5 μg/ml), $1 \times 10^6$ Listeria/ml.

One set of samples A through D received no poly(dT)-3000 and another set received a total of 2 ug of poly(dT)-3000 per sample.

The wells were incubated at 37° C. for 40 minutes with 0.5 μg/ml of the 5' biotinylated riboprobe, which labeled both Listeria and Campylobacter rRNA. At that point color was developed to measure signal strength in all samples. Table 5 shows the results.

TABLE 5

Addition of Poly (dT) to Block the Interference of Poly (dA)-containing Molecules with Capture Schemes Employing dA-tailed Probes Prehybridized to Poly (dT)-polystyrene

| Sample | OD405 Without Exogenously Added Poly (dT) | OD405 With Exogenously Added Poly (dT) |
| --- | --- | --- |
| A | 0.658 | 0.636 |
| B | 0.685 | 0.684 |
| C | 0.002 | 0.000 |
| D | 0.031 | 0.004 |

The results shown are averages of duplicate points. Note that the presence of poly(dT) in the capture had no effect on the signal generated. This is expected, provided that the solution phase poly (dT) does not displace the tailed probe from the prehybridized poly(dT). Also, note that the background in sample D was reduced about eightfold from 0.031 to 0.004 by the inclusion of poly(dT) in sample. Evidently, the added poly(dT) bound to the added poly(dA) and prevented it from binding to the small amount of free, immobilized poly(dT) (left vacant by the loss of some of the prehybridized Campylobacter tailed probe). Thus the combination of the addition of some poly(dT) to the sample and the use of a prehybridized tailed capture probe is a method that is very effective in preventing any possible increase in assay background stemming from endogenous poly(dA)-containing molecules.

It is also possible than an amount of free poly(dA) not associated with a capture probe can be added to the solid support prior to the introduction of sample, such that any free poly(dT) sequences on the support left vacant by the prebound tailed capture probe will be preblocked by the polynucleotide and be unavailable to bind endogenous poly(dA)-containing molecules. This would accomplish the same goal of preventing any possible increase in assay background.

Equivalents

Those skilled in the art will recognize or be able to ascertain, using no more than routine experimentation, many equivalents to the specific embodiments described herein. Such equivalents are intended to be encompassed by the following claims.

We claim:

1. An improved solid phase capture hybridization assay for detecting the presence of a target nucleic acid sequence wherein interference due to competitive binding of endogenous homopolynucleotides with the homopolynucleotide capture probe is reduced, said method comprising (a) affixing to a solid support a poly(dT) sequence;

(b) hybridizing a poly(dA)-tailed capture probe with the poly(dT) sequence affixed to the solid support, the poly(dA)-tailed capture probe comprising a poly(dA) sequence and a nucleic acid sequence complementary to the target nucleic acid sequence;

(c) combining under hybridizing conditions the product of (b) with (i) a sample suspected of containing the target nucleic acid sequence, and (ii) a chaotropic compound in sufficient concentration to reduce interference by competitive poly(rA) or poly (dA) binding to poly(dT) or poly(U) thereby allowing the capture probe to remain hybridized to the poly(dT) sequence affixed to the solid support; and (d) detecting the presence of the target nucleic acid sequence hybridized to the capture probe.

2. The assay of claim 1, wherein the solid support is selected from the group consisting of: polystyrene, cellulose, nitrocellulose, glass beads and magnetic beads.

3. The assay of claim 2, wherein guanidinium thiocyanate is present at a concentration of about 2.5–3.5M and step (c) is conducted at a temperature of about 37° C., and further wherein the hybridization of step (c) is allowed to continue for a period of time in minutes substantially equivalent to the number of nucleotides present in the homopolymer tail of the capture probe.

4. The assay of claim 3 wherein the poly(dA) tail of the capture probe is about 30 to 50 nucleotides in length, and hybridization to the immobilized poly(dT) is allowed to proceed for about 30–50 minutes.

5. The assay of claim 2 wherein the polystyrene solid support is a microtiter plate.

6. The assay of claim 2 wherein the polystyrene solid support is a magnetic bead; wherein guanidinium thiocyanate is present at a concentration of about 1.0M and step (c) is conducted at a temperature of about 37° C.; and further wherein the hybridization of step (c) is allowed to continue for a period of time in minutes substantially equivalent to the number of nucleotides present in the homopolymer tail of the capture probe.

* * * * *